United States Patent
Neumann

(10) Patent No.: US 12,334,205 B2
(45) Date of Patent: *Jun. 17, 2025

(54) METHODS AND SYSTEMS FOR GENERATING LIFESTYLE CHANGE RECOMMENDATIONS BASED ON BIOLOGICAL EXTRACTIONS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,231

(22) Filed: Oct. 31, 2022

(65) Prior Publication Data
US 2023/0116778 A1    Apr. 13, 2023

Related U.S. Application Data

(63) Continuation of application No. 16/824,958, filed on Mar. 20, 2020, now Pat. No. 11,545,250.

(51) Int. Cl.
  *G16H 20/30*  (2018.01)
  *G16H 20/60*  (2018.01)

(52) U.S. Cl.
  CPC .............. *G16H 20/30* (2018.01); *G16H 20/60* (2018.01)

(58) Field of Classification Search
  CPC .............................. G16H 20/30; G16H 20/60
  (Continued)

(56) References Cited

U.S. PATENT DOCUMENTS

| 10,453,356 B2 | 10/2019 | Petrov |
| 10,559,386 B1 | 2/2020 | Neumann |

(Continued)

FOREIGN PATENT DOCUMENTS

| WO | 2009117122 A2 | 9/2009 | |
| WO | WO-2019169042 A1 * | 9/2019 | ........... C12Q 1/6886 |

OTHER PUBLICATIONS

Castelein, M. L. Phyllis; Satisfaction and risk factor lifestyle modification in a phase III cardiac rehabilitation program; University of Alberta (Canada). ProQuest Dissertations Publishing, 1991. MM70223 (Year: 1991).*

*Primary Examiner* — Hiep V Nguyen
(74) *Attorney, Agent, or Firm* — Caldwell Intellectual Property Law

(57) ABSTRACT

In an aspect, a system for generating lifestyle change recommendations based on biological extractions includes a computing device designed and configured for receiving a biological extraction pertaining to a user generating, using a first machine-learning process, a plurality of lifestyle intervention combinations as a function of the biological extraction, assigning, to each lifestyle intervention combination of the plurality of lifestyle intervention combinations, a degree of projected user adherence to the lifestyle intervention combination, wherein assigning further comprises performing a second machine learning process, and selecting, from the plurality of lifestyle intervention combinations, a lifestyle intervention combination as a function of the degree of projected user adherence of the selected lifestyle intervention combination.

19 Claims, 6 Drawing Sheets

(58) Field of Classification Search
USPC .......................................................... 705/2
See application file for complete search history.

(56) References Cited

U.S. PATENT DOCUMENTS

| | | | |
|---|---|---|---|
| 2003/0208113 A1* | 11/2003 | Mault | G16H 40/63 |
| | | | 600/316 |
| 2006/0064415 A1* | 3/2006 | Guyon | G16B 40/10 |
| 2008/0195594 A1* | 8/2008 | Gerjets | G16H 15/00 |
| | | | 707/999.005 |
| 2008/0201174 A1* | 8/2008 | Ramasubramanian | |
| | | | G16H 20/10 |
| | | | 705/3 |
| 2008/0228820 A1 | 9/2008 | Kenedy et al. | |
| 2017/0286622 A1 | 10/2017 | Cox et al. | |
| 2018/0261329 A1 | 9/2018 | Blander et al. | |
| 2018/0272065 A1 | 9/2018 | Talbot et al. | |
| 2018/0315499 A1 | 11/2018 | Appelbaum et al. | |
| 2018/0361203 A1 | 12/2018 | Wang et al. | |
| 2019/0062811 A1 | 2/2019 | Hjorth et al. | |
| 2019/0074080 A1* | 3/2019 | Appelbaum | G16H 80/00 |
| 2019/0267128 A1 | 8/2019 | Decombel et al. | |
| 2020/0005928 A1 | 1/2020 | Daniel | |

\* cited by examiner

METHODS AND SYSTEMS FOR GENERATING LIFESTYLE CHANGE RECOMMENDATIONS BASED ON BIOLOGICAL EXTRACTIONS

CROSS-REFERENCE TO RELATED APPLICATIONS

This application is a continuation of Non-provisional application Ser. No. 16/824,958 filed on Mar. 20, 2020, and entitled "METHODS AND SYSTEMS FOR GENERATING LIFESTYLE CHANGE RECOMMENDATIONS BASED ON BIOLOGICAL EXTRACTIONS," the entirety of which is incorporated herein by reference.

FIELD OF THE INVENTION

The present invention generally relates to the field of artificial intelligence. In particular, the present invention is directed to methods and systems for generating lifestyle change recommendations based on biological extractions.

BACKGROUND

Significant constitutional improvements can result from lifestyle modifications but identifying a maximally effective set thereof can be a complex task fraught with uncertainty. This problem is compounded by the fact that effects can vary depending on underlying circumstances, such that an ideal solution in one situation may fall short in another.

SUMMARY OF THE DISCLOSURE

In an aspect, a system for generating lifestyle change recommendations based on biological extractions, the system including a computing device, the computing device designed and configured to receive a biological extraction pertaining to a user, wherein the biological extraction includes user physiological data including responses to a questionnaire. The computing device further configured to generate, using a first machine-learning process, a plurality of lifestyle intervention combinations as a function of the biological extraction, wherein generating the plurality of lifestyle intervention combinations further includes training a first machine-learning model using a first training data set and the first machine-learning process, wherein the first training data set includes entries correlating biological extraction data with lifestyle intervention combinations. The computing device further configured to derive a user inclination enumeration as a function of at least a user input. The computing device further configured to assign, using a second machine-learning process, to each lifestyle intervention combination of the plurality of lifestyle intervention combinations, a projected degree of user adherence as a function of the user inclination enumeration. The computing device further configured to select, from the plurality of lifestyle intervention combinations, a lifestyle intervention combination as a function of the projected degree of user adherence of the selected lifestyle intervention combination.

In another aspect, a method for generating lifestyle change recommendations based on biological extractions, the method including receiving, by a computing device, a biological extraction pertaining to a user, wherein the biological extraction includes user physiological data including responses to a questionnaire. The method including generating, by the computing device using a first machine-learning process, a plurality of lifestyle intervention combinations as a function of the biological extraction, wherein generating the plurality of lifestyle intervention combinations further includes training a first machine-learning model using a first training data set and the first machine-learning process, wherein the first training data set includes entries correlating biological extraction data with lifestyle intervention combinations. The method including deriving, by the computing device, a user inclination enumeration as a function of at least a user input. The method including assigning, by the computing device using a second machine-learning process, to each lifestyle intervention combination of the plurality of lifestyle intervention combinations, a projected degree of user adherence as a function of the user inclination enumeration. The method including selecting, by the computing device, from the plurality of lifestyle intervention combinations, a lifestyle intervention combination as a function of the projected degree of user adherence of the selected lifestyle intervention combination.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments disclosed herein generate lifestyle interventions, and combinations thereof, that are potentially beneficial given a user's biological extraction, using one or more machine-learning processes. Projections of likely user adherence to such intervention combinations may be determined using further machine-learning or classification processes. Combinations may be filtered according to user restrictions.

Figure 1:
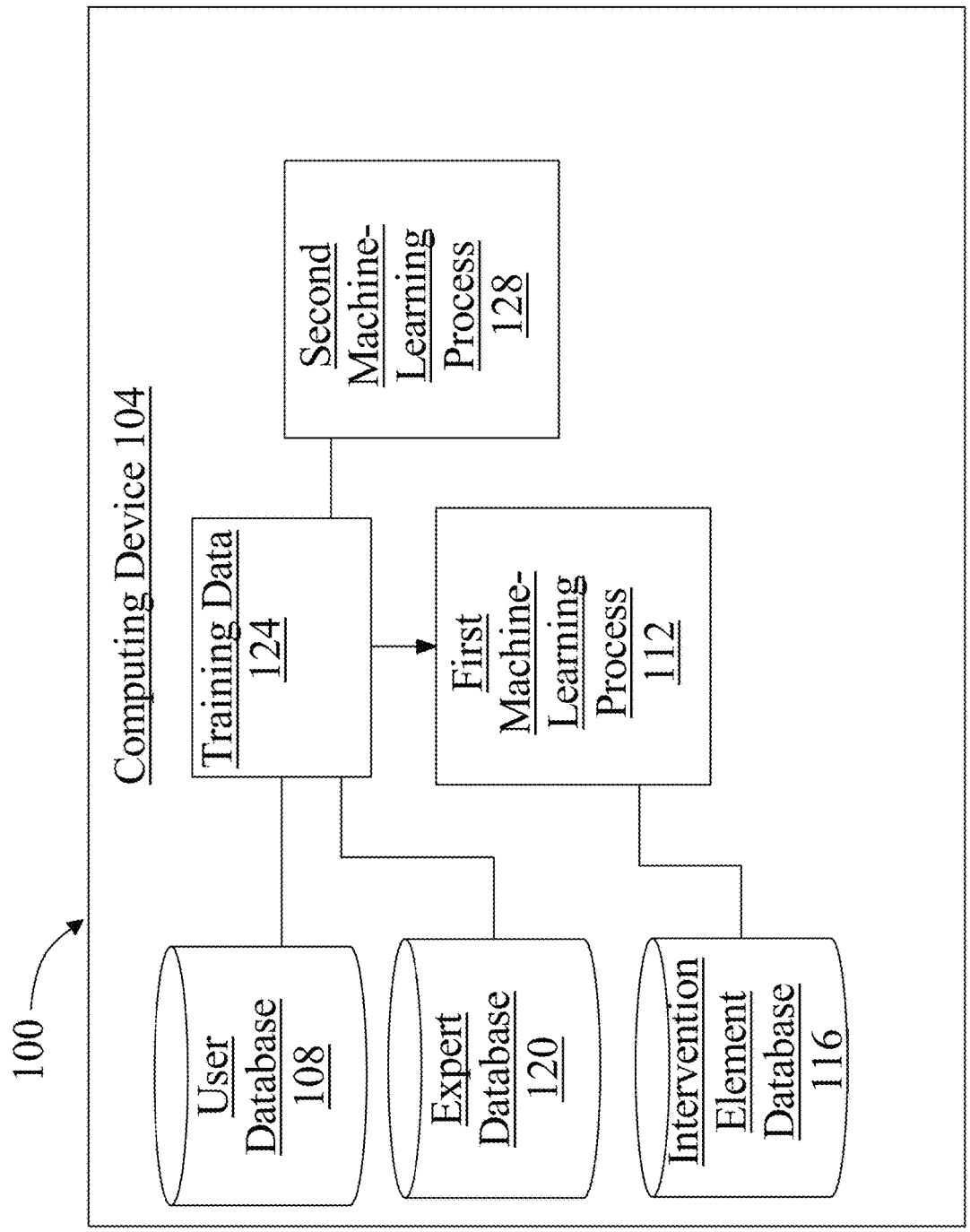
FIG. 1 is a block diagram of an exemplary embodiment of a system for generating lifestyle change recommendations based on biological extractions.

Referring now to FIG. 1, an exemplary embodiment of a system 100 for generating lifestyle change recommendations based on biological extractions is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is designed and configured to receive a biological extraction pertaining to a user. A "biological extraction" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement of blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices 104; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a *Microbiome* of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, *Microbiome*, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, and blood clotting factors.

With continued reference to FIG. 1, gut-wall body measurement may include one or more stool test results describing presence or absence of parasites, *Firmicutes, Bacteroidetes*, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *Cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-300. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, *Microbiome*, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. *Microbiome* may include for example, bacteria, archaea, protists, fungi, and viruses. *Microbiome* may include commensal organisms that exist within a human being without causing harm or disease. *Microbiome* may include organisms that are not harmful but rather harm the human when they produce toxic metabolites such as trimethylamine. *Microbiome* may include pathogenic organisms that cause host damage through virulence factors such as producing toxic by-products. *Microbiome* may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies'* and *Methanosphaera stadtmanae*. Fungi may include *Candida* species and *Malassezia* species. Viruses may include bacteriophages. *Microbiome* species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, *Microbiome* body measurement may include one or more stool test results describing presence, absence, and/or measurement of microorganisms including bacteria, archaea, fungi, protozoa, algae, viruses, parasites, worms, and the like. Stool test results may contain species such as *Ackerman's muciniphila, Anaerotruncus colihominis*, bacteriology, *Bacteroides vulgates', Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, *Microbiome* body measurement may include one or more stool tests results that identify all microorganisms living a user's gut including bacteria, viruses, archaea, yeast, fungi, parasites, and bacteriophages. *Microbiome* body measurement may include DNA and RNA sequences from live microorganisms that may impact a user's health. *Microbiome* body measurement may include high resolution of both species and strains of all microorganisms. *Microbiome* body measurement may include data describing current microbe activity. *Microbiome* body measurement may include expression of levels of active microbial gene functions. *Microbiome* body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, *Microbiome* body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, *Microbiome* body measurement may include one or more breath test results that identify certain strains of microorganisms that may be present in certain areas of a user's body. This may include for example, lactose intolerance breath tests, methane-based breath tests, hydrogen-based breath tests, fructose-based breath tests, *Helicobacter pylori* breath test, fructose intolerance breath test, bacterial overgrowth syndrome breath tests and the like.

With continued reference to FIG. 1, *Microbiome* body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor.

Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vasodilation and vasoconstriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100. User data may include a profile, such as a psychological profile, generated using previous item selections by the user; profile may include, without limitation, a set of actions and/or navigational actions performed as described in further detail below, which may be combined with biological extraction data and/or other user data for processes as described in further detail below.

Physiological data and/or other data of each user may be stored, without limitation, in a user database 108. User database 108 may include any data structure for ordered storage and retrieval of data, which may be implemented as a hardware or software module. A user database 108 may be implemented, without limitation, as a relational database, a key-value retrieval datastore such as a NOSQL database, or any other format or structure for use as a datastore that a person skilled in the art would recognize as suitable upon review of the entirety of this disclosure. A user database 108 may include a plurality of data entries and/or records corresponding to user tests as described above. Data entries in a user database 108 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 108 may reflect categories, cohorts, and/or populations of data consistently with this disclosure. User database 108 may be located in memory of computing device 104 and/or on another device in and/or in communication with system 100.

Figure 2:
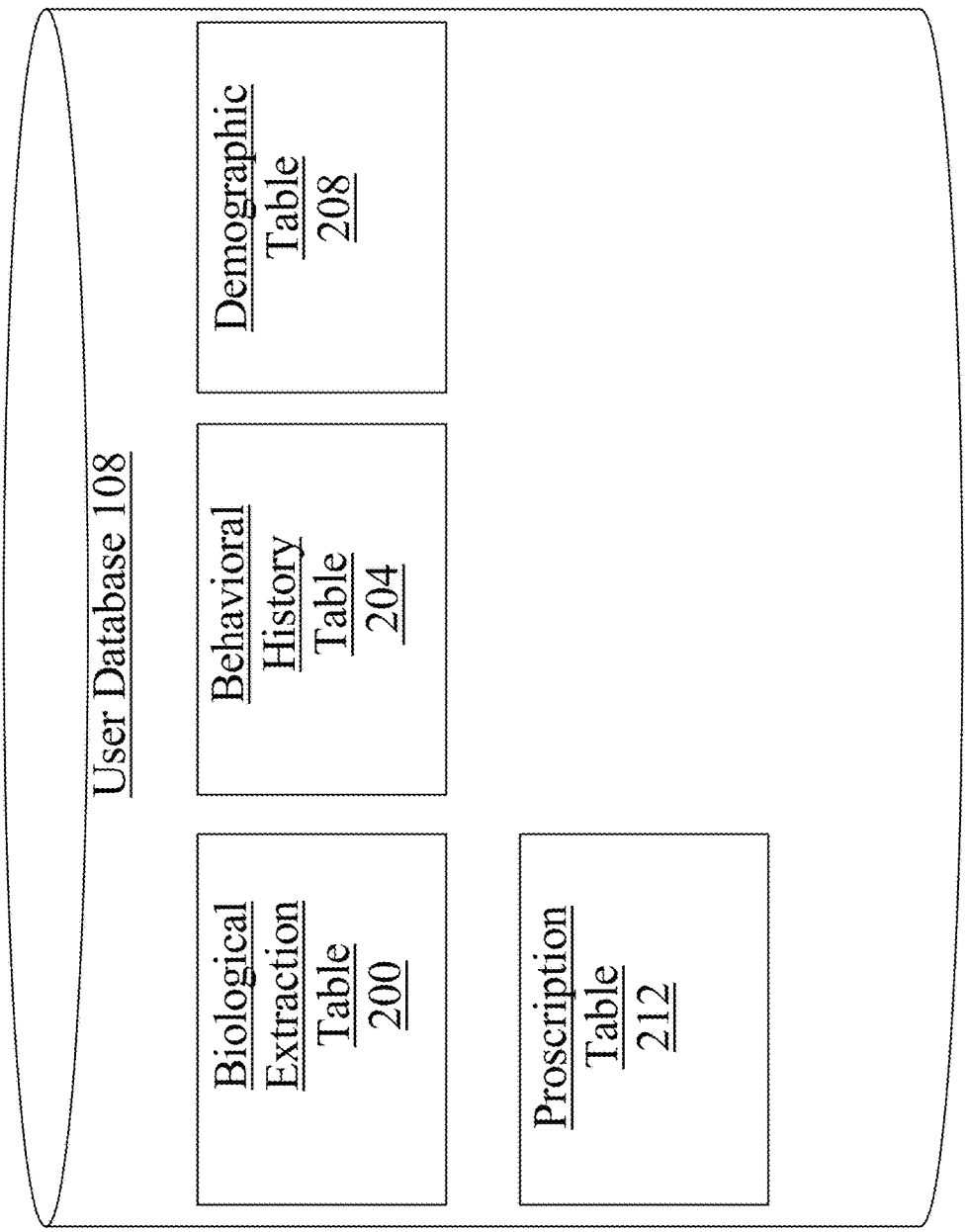
FIG. 2 is a block diagram of an exemplary embodiment of a user database.

Referring now to FIG. 2, an exemplary embodiment of a user database 108 is illustrated. One or more tables in user database 108 may include, without limitation, a biological extraction table 200, which may be used to store biological extraction data. User database 108 may include a behavioral history table 204, where current or past reports or information indicative of user behavior, including without limitation negative lifestyle behaviors, may be stored; behavioral history table 204 may store, as a non-limiting example, records of reports received from user and/or other persons and/or devices indicating engagement in one or more negative lifestyle behaviors as described in this disclosure. User database 108 may include a demographic table 112, which may include a demographic table 208; demographic table may include any demographic information concerning a user, including without limitation age, sex, national origin, ethnicity, language, religious affiliation, and the like. User database 108 may include a proscription table 112, which may store one or more user proscriptions and/or user belief proscriptions as described in further detail below. Persons skilled in the art, upon reviewing the entirety of this disclosure, will be aware of various alternative or additional data which may be stored in user database 108, including without limitation any data concerning any user activity, demographics, profile information, viewing and/or media consumption history, or the like.

Still referring to FIG. 1, computing device 104 is designed and configured to generate a plurality of lifestyle intervention combinations as a function of biological extraction using a first machine-learning process 112. A "lifestyle intervention combination" is a set of actions, called "intervention elements," a user can take that, taken together, act to improve the user's physical condition. Each such intervention element may be stored in an intervention element database 116, which may be implemented in any manner suitable for implementation of user database 108 as described above.

Figure 3:
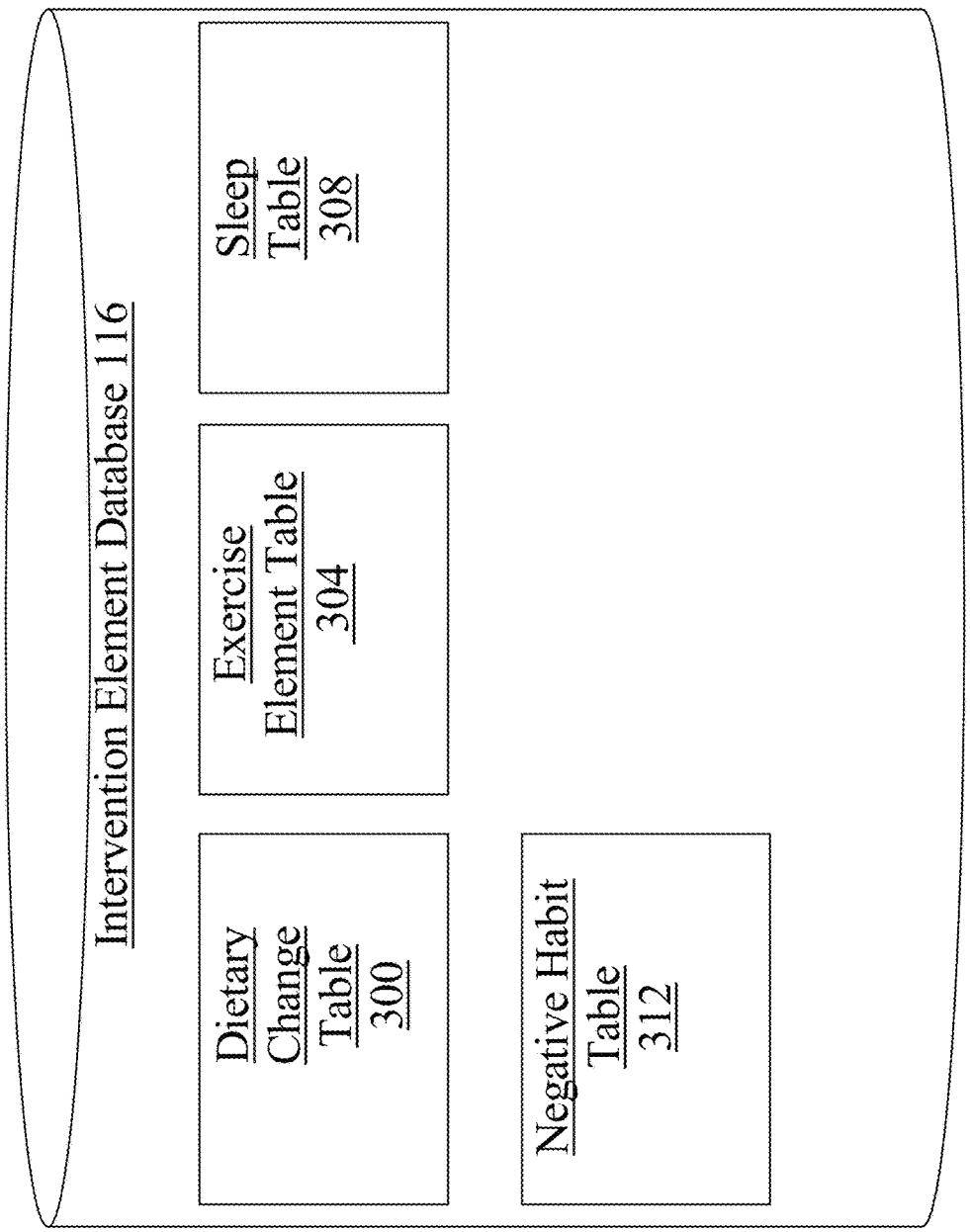
FIG. 3 is a block diagram of an exemplary embodiment of an intervention database.

Referring now to FIG. 3, an exemplary embodiment of intervention element database 116 is illustrated. Intervention element database 116 may include a dietary change table 300, which may contain, without limitation, intervention elements corresponding to dietary changes, such as without limitation a reduction in the daily consumption of a particular nutrient, an increase in the daily consumption of a particular nutrient, a decrease in the daily consumption of a given category of food, an increase in the daily consumption of a given category of food, or the like. For instance, and without limitation, an intervention element may include cessation of meat consumption, an addition of one serving of fruit per day, a halving of daily saturated fat intake as measured in calories and/or grams of saturated fat, or the like. Intervention elements pertaining to nutritional goals may list particular meals, meal plans, food elements, or the like, together with corresponding nutritional goals met by such meals, meal plans, and/or food elements. Intervention element database 116 may include an exercise element table 304, which may contain intervention elements that include one or more measurable exercise goals, such as a goal to take some target number of steps per day, a goal to burn a target number of calories per day, a goal to engage in a certain amount of cardiovascular exercise at a given intensity level, as represented for instance by a number on a discrete scale from 1 to 10, where 1 is a minimal intensity and 10 is a maximal intensity, a goal to engage in a certain amount of resistance training at a given intensity level, which may be similarly represented, a goal to spend a certain quantity of time per day stretching, or the like. Intervention elements pertaining to exercise goals may include particular forms of exercise, such as jogging, biking, weightlifting, or the like, which may list corresponding exercise goals that match the intervention elements. Intervention element database 116 may include, without limitation, a sleep table 308, which may record one or more intervention elements to sleep goals, such as a goal to sleep a certain number of hours per week or per day, to set a fixed bedtime, or the like. Intervention element table may include, without limitation, a negative habit table 312, which may record information elements relating to a cessation or reduction of a negative habit, such as tobacco consumption, alcohol consumption, gambling, drug use, or the like; such intervention elements may alternatively or additionally list particular programs and/or protocols for reduction in bad habits, such as 12-step programs or the like.

Referring again to FIG. 1, computing device 104 may generate each lifestyle intervention combination of plurality of lifestyle intervention combinations by combining intervention elements, which may be retrieved from intervention element database 116. Intervention elements for combinations may be selected according to intervention elements likely to improve a particular user's state of health; such elements may be identified, without limitation, using expert inputs; for instance expert inputs may link particular endocrinal levels and/or change in endocrinal levels to particular nutritional goals, exercise goals, sleep goals, or cessation of bad habits, which may in turn be used to retrieve particular intervention elements from intervention element database 116. As another non-limiting example, one or more expert inputs may identify reductions in bad habits that may improve user health, one or more programs that may aid in cessation of one or more bad habits, or the like. One or more expert inputs may propose one or more combinations of intervention elements that an expert may opine are especially useful, and/or that an expert may have viewed in the past as efficacious or convenient. Expert opinions may be stored in and/or retrieved from an expert database 120, which may include any component and/or module suitable for use as user database 108 as described above.

Figure 4:
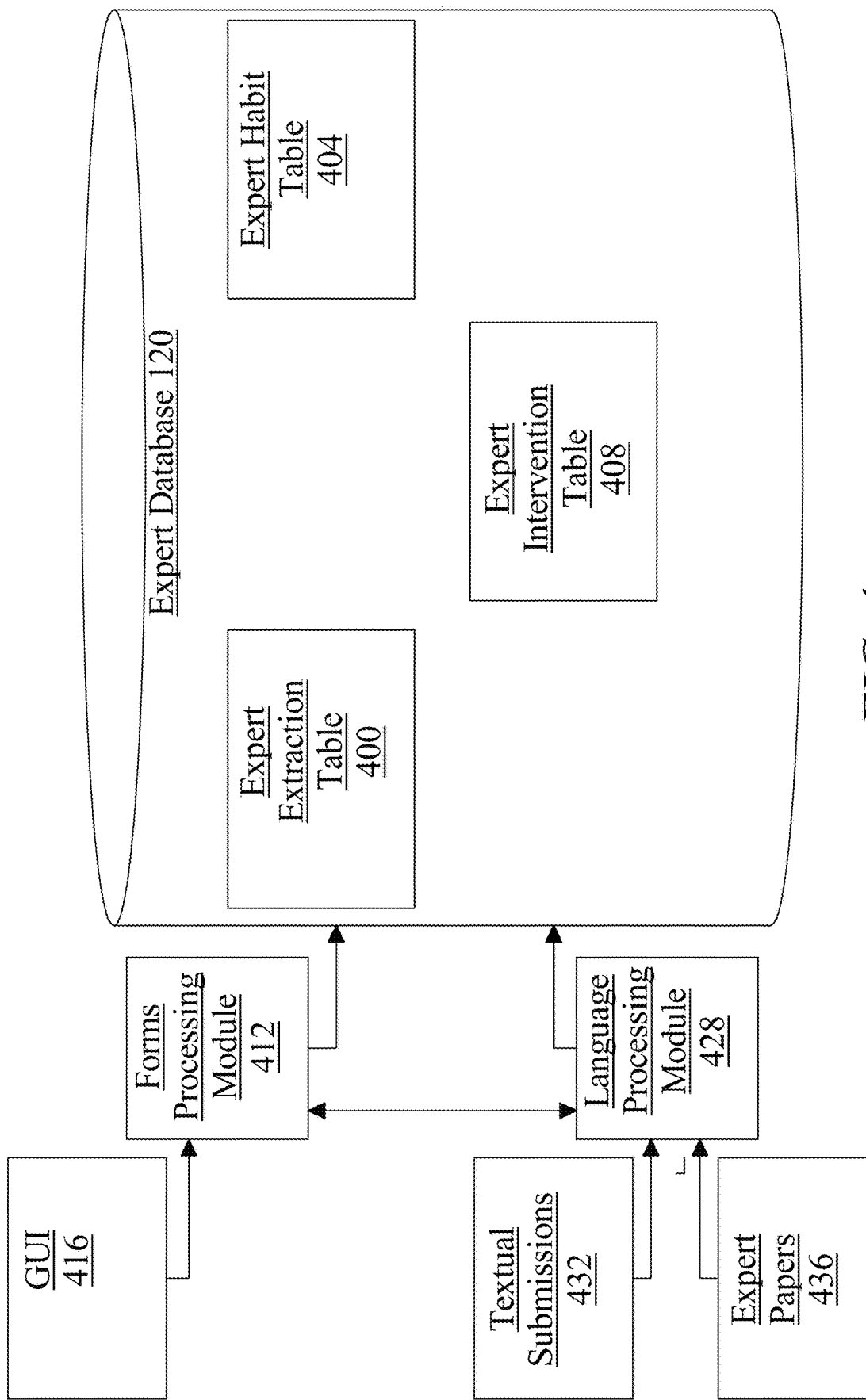
FIG. 4 is a block diagram of an exemplary embodiment of an expert database.

Referring now to FIG. 4, an exemplary embodiment of an expert database 120 is illustrated. Expert database 120 may, as a non-limiting example, organize data stored in the expert database 120 according to one or more database tables. One or more database tables may be linked to one another by, for instance, common column values. For instance, a common column between two tables of expert database 120 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert database 120 may include, as a non-limiting example, an expert extraction table 400, which may record expert submission data corresponding to biological extraction data as described above. Tables may include an expert habit table 404, which may record expert submission data describing one or more negative lifestyle habits as described in further detail below, as well as relationships thereof with biological extractions. Tables may include an expert intervention table 408, which may record expert submission data describing one or more intervention elements and/or lifestyle intervention combinations as described in above, as well as relationships thereof with biological extractions and/or negative lifestyle habits.

In an embodiment, and still referring to FIG. 4, a forms processing module 412 may sort data entered in a submission via a graphical user interface 416 receiving expert submissions by, for instance, sorting data from entries in the graphical user interface 416 to related categories of data; for instance, data entered in an entry relating in the graphical user interface 416 to endocrinal data may be sorted into variables and/or data structures for endocrinal data, which may be provided to expert endocrinal table, while data entered in an entry relating to telomere length may be sorted into variables and/or data structures for the storage of, telomere length data, such as expert telomeric table. Where data is chosen by an expert from pre-selected entries such as drop-down lists, data may be stored directly; where data is entered in textual form, a language processing module 428 may be used to map data to an appropriate existing label, for instance using a vector similarity test or other synonym-sensitive language processing test to map data to existing labels and/or categories. Similarly, data from an expert textual submissions 432, such as accomplished by filling out a paper or PDF form and/or submitting narrative information, may likewise be processed using language processing module 428.

Still referring to FIG. 4, a language processing module 428 may include any hardware and/or software module. Language processing module 428 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 4, language processing module 428 may compare extracted words to categories of data to be analyzed; such data for comparison may be entered on computing device 104 as described above using expert data inputs or the like. In an embodiment, one or more categories may be enumerated, to find total count of mentions in such documents. Alternatively or additionally, language processing module 428 may operate to produce a language processing model. Language processing model may include a program automatically generated by at least a server and/or language processing module 428 to produce associations between one or more words extracted from at least a document and detect associations, including without limitation mathematical associations, between such words, and/or associations between such words and other elements of data analyzed, processed and/or stored by system 100. Associations between language elements, may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of data; positive or negative indication may include an indication that a given document is or is not indicating a category of data.

Still referring to FIG. 4, language processing module 428 and/or computing device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 428 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 4, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 4, language processing module 428 may use a corpus of documents to generate associations between language elements in a language processing module 428, and computing device 104 may then use such associations to analyze words extracted from one or more documents. Documents may be entered into classification device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, classification device 104 may automatically obtain the document using such an identifier, for instance by submitting a request to a database or compendium of documents such as JSTOR as provided by Ithaka Harbors, Inc. of New York.

Data may be extracted from expert papers 436, which may include without limitation publications in medical and/or scientific journals, by language processing module 428 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Referring again to FIG. 1, computing device is configured to generate a plurality of lifestyle intervention combinations as a function of biological extraction using first machine-learning process 112. A machine learning process is a process that automatically uses a body of data known as "training data 124" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 1, training data 124, as used herein, is data containing correlations that a machine-learning process may use to model relationships between two or more categories of data elements. For instance, and without limitation, training data 124 may include a plurality of data entries, each entry representing a set of data elements that were recorded, received, and/or generated together; data elements may be correlated by shared existence in a given data entry, by proximity in a given data entry, or the like. Multiple data entries in training data 124 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 124 according to various correlations; correlations may indicate causative and/or predictive links between categories of data elements, which may be modeled as relationships such as mathematical relationships by machine-learning processes as described in further detail below. Training data 124 may be formatted and/or organized by categories of data elements, for instance by associating data elements with one or more descriptors corresponding to categories of data elements. As a non-limiting example, training data 124 may include data entered in standardized forms by persons or processes, such that entry of a given data element in a given field in a form may be mapped to one or more descriptors of categories. Elements in training data 124 may be linked to descriptors of categories by tags, tokens, or other data elements; for instance, and without limitation, training data 124 may be provided in fixed-length formats, formats linking positions of data to categories such as comma-separated value (CSV) formats and/or self-describing formats such as extensible markup language (XML), enabling processes or devices to detect categories of data.

Alternatively or additionally, and continuing to refer to FIG. 1, training data 124 may include one or more elements that are not categorized; that is, training data 124 may not be formatted or contain descriptors for some elements of data. Machine-learning algorithms and/or other processes may sort training data 124 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 124 to be made applicable for two or more distinct machine-learning algorithms as described in further detail below. Training data 124 used by computing device may correlate any input data as described in this disclosure to any output data as described in this disclosure. As a non-limiting illustrative example, training data 124 may correlate biological extraction data and/or physiological data as inputs to lifestyle intervention combinations and/or intervention elements. Such entries may be provided by expert entries and/or from expert database 120s, and/or include entries by users and/or by system 100 indicating efficacy of lifestyle intervention combinations for persons from whom biological extractions were received. Persons skilled in the art, upon reviewing the entirety of this disclosure, will be aware of various elements that may be correlated and/or included together in elements of training data 124 as consistent with this disclosure.

Still referring to FIG. 1, computing device 104 may be designed and configured to perform first machine-learning process 112 in any suitable manner. For instance, and without limitation, computing device 104 may create a machine-learning model using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include biological extractions and/or physiological data as described above as inputs, lifestyle intervention combinations and/or intervention elements as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 124. Persons skilled in the art, upon reviewing the entirety of this disclosure, will be aware of various possible variations of supervised machine learning algorithms that may be used to determine relation between inputs and outputs.

Supervised machine-learning processes may include classification algorithms, defined as processes whereby a computing device derives, from training data 124, a model for sorting inputs into categories or bins of data. Classification may be performed using, without limitation, linear classifiers such as without limitation logistic regression and/or naive Bayes classifiers, nearest neighbor classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training data 124 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

A machine-learning process may include a lazy-learning process. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 124. Heuristic may include selecting some number of highest-ranking associations and/or training data 124 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, and as a non-limiting example, generating plurality of lifestyle intervention combinations may include performing a machine-learning process that generates lifestyle intervention combinations and/or intervention elements from biological extraction data; for instance, and without limitation, computing device may generate a machine-learning model using first machine-learning process 112 and training data 124 having entries correlating biological extract data and/or physiological data with lifestyle intervention combinations and/or intervention elements, producing a machine-learning model that inputs biological extraction and outputs a plurality of lifestyle intervention combinations and/or intervention elements.

Still referring to FIG. 1, generating the plurality of lifestyle intervention combinations may alternatively or additionally include receiving a description of at least a current disease state of the user and generating the plurality of lifestyle intervention combinations as a function of the current disease state. As used in this disclosure a "current disease state" includes any current, nascent, and/or probable future medical condition based on biological extractions, for instance as may be denoted by a prognostic label as described in U.S. Nonprovisional application Ser. No. 16/372,512, dated Apr. 2, 2019, and entitled "METHODS AND SYSTEMS FOR UTILIZING DIAGNOSTICS FOR INFORMED VIBRANT CONSTITUTIONAL GUIDANCE," The entirety of which is incorporated by reference in this disclosure. Identification of a current disease state may be received from a device operated by user, such as without limitation a personal computer, mobile device, or the like. Alternatively or additionally, identification of a current disease state may be received from a third-party device such as from a doctor or other medical professional, family member, friend, partner, or the like. In a further non-limiting example, current disease state may be determined from biological extraction using database lookup and/or machine-learning methods, for instance and without limitation as described in U.S. Nonprovisional application Ser. No. 16/372,512.

Still referring to FIG. 1, generation of lifestyle intervention combinations using current disease state may include generating a machine-learning model and/or executing a machine learning process that takes current disease state as an input and outputs a plurality of lifestyle intervention combinations and/or intervention elements, for instance as described in U.S. Nonprovisional application Ser. No. 16/372,512.

Further referring to FIG. 1, generating the plurality of lifestyle intervention combinations may include identifying a negative lifestyle behavior of the user. A negative lifestyle behavior may include a habit and/or behavior a user is engaged in that tends to act to the detriment of the user's health. A habit a user is engaged in may be a nutritional habit, such as a daily consumption of sugar, fat, fiber, protein, or the like. A habit a user is engaged in may include an exercise habit, which may be measured in terms of a duration per day, week, or the like of cardiovascular exercise, resistance training exercise, or other exercise category, a number of steps per week taken, resting and/or total calorie consumption numbers, or the like. A habit a user is engaged in may include a substance abuse habit, including some measure of a dosage per period of time consumed of a harmful and/or addictive substance such as an opiate, alcohol, tobacco, stimulants such as cocaine, methamphetamine or the like, hallucinogens, narcotics, or other mood-altering chemicals. A habit a user is engaged in may include a sleep habit, including a number of hours per night a user sleeps, a number of nights a user goes with less than a recommended amount of sleep, or the like.

Still referring to FIG. 1, computing device 104 may receive information identifying a negative lifestyle behavior from a device operated by user; for instance, user may provide the input after a lapse in self-control. Negative lifestyle behavior may be identified by a user entry; for instance, and without limitation, computing device 104 may provide a user with a questionnaire in the form of one or more data fields requesting that the user identify activities in which the user engaged. Questions presented to a user may include a number of servings of alcohol a user consumes during a given period of time such as a day, a week or a year, a quantity of tobacco, drugs, or other substances that a user consumes during a given period of time, a number of hours a user sleeps in a night, or the like. A user may respond to such questions by selecting options corresponding to particular ranges of data, by setting sliders or other indicators of a quantity along a continuous range, by entering values in drop-down lists, and/or by typing in numbers or text. Alternatively or additionally, another person, potentially from a different remote device, may report that user has engaged in the negative lifestyle behavior. For instance, a family member, neighbor, spouse, boyfriend, girlfriend, ex-boyfriend, ex-girlfriend, religious leader, co-worker, or the like may observe user engaging in negative lifestyle behavior, such as a drinking binge, a pattern of overeating, a tendency to sessile behavior, or the like. Computing device 104 may track such notifications and/or compare such notifications to negative behavioral propensities. For instance, computing device 104 may record a first such report as indicative that user is at an elevated risk to engage in negative lifestyle behavior. In an embodiment, one or more words and/or phrases entered by a user, who may include any user as described above, may be mapped to a label, or particular word or phrase used by computing device 104 to describe an object, behavior, negative lifestyle behavior, negative behavioral tendency, or the like, using a language processing model, module, and/or algorithm as described above; for instance, computing device 104 may determine using a language processing model, module, and/or algorithm as described above that the word or phrase entered by the user is a synonym of the label, and may substitute the label for the word or phrase.

Alternatively or additionally, identifying negative lifestyle behavior may include receiving a training set correlating biological extractions to negative lifestyle behaviors, generating negative behavior identifier model using a supervised machine-learning algorithm and the training set, producing a negative lifestyle behavior output from the negative behavior identifier model using the biological extraction, and identifying the negative lifestyle behavior as a function of the negative behavior output. Training set may correlate biological extractions to negative lifestyle behaviors by matching biological extraction data of individual who self-report particular negative habits; training set entries may alternatively or additionally be provided by expert submissions as described above. Identifying a negative lifestyle behavior may include generating a negative lifestyle behavior identifier model using a supervised machine-learning algorithm and the training set; negative habit identifier model may be generated, without limitation, using a classification algorithm, so that negative habit identifier may match biological extraction data to a most likely habit or a set of most likely habits of which user may partake. Identifying a negative lifestyle behavior may include producing a negative habit output from the negative habit identifier model using biological extraction data and identifying the negative lifestyle behavior as a function of the negative habit output.

Still referring to FIG. 1, classification algorithm used as above to identify a negative lifestyle behavior may generate a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data 124. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data 124 into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data 124 to classify input data to one or more clusters and/or categories of features as represented in training data 124; this may be performed by representing both training data 124 and input data in vector forms, and using one or more measures of vector similarity to identify classifications within training data 124, and to determine a classification of input data. K-nearest neighbors algorithm may include specifying a K-value, or a number directing the classifier to select the k most similar entries training data 124 to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data 124. Heuristic may include selecting some number of highest-ranking associations and/or training data 124 elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data 124 are represented by different quantities of samples, which may result in proportionally equivalent vectors with divergent values.

With continued reference to FIG. 1, computing device 104 may generate a plurality of lifestyle intervention combinations as a function of and/or based on the negative lifestyle behavior. Each lifestyle intervention combination may alleviate negative lifestyle behavior; in other words, each lifestyle intervention may include intervention components tending to counteract negative effects of negative lifestyle behavior, either by reducing and/or ceasing the negative lifestyle behavior and/or by acting to reduce negative health effects thereof. For example, alleviation of a negative lifestyle behavior including a sedentary lifestyle may include an exercise program and/or a dietary change reducing caloric intake to reduce risk of weight gain. As a further example alleviation of a negative lifestyle behavior including overconsumption of simple sugars may include an instruction to consume fewer sugars, for instance by using sugar substitutes, and/or may recommend an increase in exercise and/or consumption of foods tending to lower glycemic index to reduce the impact of the additional sugar on the body.

Still referring to FIG. 1, computing device 104 may perform one or more machine-learning processes, as described above, to generate a plurality of lifestyle intervention combinations based on negative lifestyle behavior. For instance, and without limitation, first machine-learning process 112 may include a first process and/or model generating negative lifestyle behavior from biological extraction data and a second process and/or model generating lifestyle intervention combinations as a function of negative lifestyle behavior; the latter may be trained, without limitation, using training data 124 having entries correlating negative lifestyle behaviors and lifestyle interventions and/or intervention elements tending to alleviate negative lifestyle behaviors, which may be assembled, received, and/or aggregated using any methods above, including without limitation user entries, case histories, and/or expert submissions. As a further non-limiting example, first machine-learning process 112 may include a machine learning process generating lifestyle intervention combinations and/or intervention elements from combinations of biological extraction data negative lifestyle behavior data; the latter may be trained, without limitation, using training data 124 having entries correlating combinations negative lifestyle behaviors and biological extraction with lifestyle interventions and/or intervention elements tending to alleviate negative lifestyle behaviors and/or conditions and/or risks associated with biological extractions such as biomarkers indicative of elevated heart disease risk or the like, which may be assembled, received, and/or aggregated using any methods above, including without limitation user entries, case histories, and/or expert submissions. As a further non-limiting example, first machine-learning process 112 generate lifestyle intervention combinations and/or intervention elements from biological extraction data and a second process and/or model may lifestyle intervention combinations as a function of negative lifestyle behavior, where the latter may be trained, without limitation, using training data 124 having entries correlating negative lifestyle behaviors and lifestyle interventions and/or intervention elements tending to alleviate negative lifestyle behaviors, which may be assembled, received, and/or aggregated using any methods above, including without limitation user entries, case histories, and/or expert submissions; the output of the first machine-learning process 112 and second machine-learning process 128 may be combined to produce an aggregate output, which may, for instance, be made up of the intersection of the output of the first machine-learning process 112 and the second machine-learning process 128, a combination of all elements of both processes, or the like, any of which aggregate outputs may be ranked according to any process provided herein for ranking results.

With continued reference to FIG. 1, results as described above relating to negative lifestyle behaviors may be combined in any manner described above with results relating to current disease states, for instance by aggregation as described above with such results and/or by performance of one or more machine-learning processes, as described above, using training data 124 relating any combination of biological extraction data, current disease state data, and/or negative lifestyle behavior data to any combination of lifestyle intervention combinations, intervention elements, current disease states, and/or negative lifestyle behaviors.

Still referring to FIG. 1, computing device 104 is configured to assign, to each lifestyle intervention combination of plurality of lifestyle intervention combinations, a degree of projected user adherence to the lifestyle intervention combination, using a second machine-learning process 128. A "degree of adherence," as used in this disclosure, is a degree to which a user performs a recommended lifestyle intervention combination; a "projected degree of adherence" is an estimated degree of adherence to a lifestyle intervention combination in the future. A degree of adherence and/or projected degree of adherence may include a quantitative measure such as a score, a percentage of adherence, or the like. Assigning includes performing a second machine learning process, which may include any machine-learning process as described above.

In an embodiment, and still referring to FIG. 1, assigning the degree of projected user adherence may include providing a user inclination enumeration, determining, using a classifier, a distance from the user inclination enumeration to each lifestyle intervention combination of the plurality of lifestyle intervention combinations, and assigning the degree of projected user adherence using the distance. A "user inclination enumeration," as used in this disclosure, is a data structure that represents a quantitative measure of a degree of importance a user places on each of a plurality of intervention elements; quantitative measures may be used to express both fondness for and aversion to intervention elements, such as without limitation by describing aversion with negative values and fondness with positive values, or any suitable alternative approach therefor that may occur to a person skilled in the art upon reviewing the entirety of this disclosure. A user inclination enumeration may include an n-tuple of values, where n is at least two values, as described in further detail below. Each value of n-tuple of values may represent a measurement or other quantitative value associated with a given category of data, or attribute, examples of which are provided in further detail below; n-tuple may be represented, without limitation, as a vector in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance be advantageous where each vector represents a weighing of user priorities, and/or is to be compared to such a weighing of user inclinations.

Continuing to refer to FIG. 1, user inclination enumeration may include a plurality of entries, which are attributes of user inclination enumeration as described above. Entries may include, without limitation, an attribute indicating a degree of importance to user of cost of an action that may be taken to improve health, alleviate a current disease state, and/or mitigate effects of a negative lifestyle behavior, such as an intervention and/or intervention element as described above; for instance, an entry may indicate a strong aversion to high-intensity exercise and/or one or more categories thereof, while another entry may indicate a slight fondness for low-intensity exercise such as walking or yoga, or the like. As another non-limiting example, an entry may indicate an aversion to a given kind of food and/or dietary elimination; for instance a user may be averse to removal of carbohydrates from the user's diet, while being relatively accepting of a portion-control protocol and/or an increase in consumption of vegetables.

Referring again to FIG. 1, computing device 104 may derive user inclination enumeration by receiving at least a user input. For instance, a graphical user interface 416 may display at user device options to rate one or more priorities absolutely and/or relatively to each other, for instance by providing a numerical rating scale with radio buttons and/or drop-down lists, sliders where a user may set relative importance along a continuum for each user inclination enumeration attribute, and/or textual entry fields wherein a user may enter numbers reflecting user's personal degree of fondness and/or aversion for an intervention element corresponding to each field.

Alternatively or additionally, and still referring to FIG. 1, deriving the user inclination enumeration may include generating a default enumeration; a default enumeration may contain default values that represent a "first guess" by system 100 for what user's relative priorities, likes, and/or dislikes are likely to be. Default enumeration may be stored in and/or retrieved from expert database 120, which may be populated based on an expert determination of likely priorities. Alternatively, a person acquainted with user may enter, in a display as described above, what that person believes user's priorities are likely to be; multiple such entries may be aggregated, averaged, or the like. In an embodiment, computing device 104 may use a machine-learning process to generate a default enumeration; this may be performed by predicting a user's likely priorities and/or preferences based on previously determined priorities and/or preferences of another person. For instance, generating a default enumeration may include receiving a default enumeration training set correlating a cohort of individual information to individual user inclination enumerations. Default enumeration training set may include a plurality of entries, each entry corresponding to a different person; entries may be anonymized to preserve individual privacy. Each entry of plurality of entries may include a set of personal data, pertaining to a person represented by the entry, which may include any information suitable for inclusion in user database 108 as described above, including user preferences, habits, health information including without limitation biological extraction data, negative lifestyle behavior data, user demographic data, and the like. Each entry may also include a user inclination enumeration, which may include any element and/or elements suitable for inclusion in user inclination enumeration as described above.

Still referring to FIG. 1, computing device 104 may generating a set of user data regarding the user; set of user data may be generated to match categories of data in entries in default enumeration training set. In an embodiment set of user data may be generated by querying user database 108. Alternatively or additionally, one or more elements of set of user data may be obtained by prompting user to enter the one or more elements at a user device and receiving the one or more elements in response to the prompting; one or more elements may be obtained, alternatively or additionally, by prompting another person, for instance at or via an additional client device, to provide the one or more elements of data, and receiving the one or more elements in response. The above-described methods may be combined; for instance, computing device 104 may query user database 108 to obtain some elements of user data, determine that one or more elements matching categories in default enumeration database are missing, and prompt user and/or another person to provide such elements. Persons skilled in the art, upon reviewing the entirety of this disclosure, will be aware of various ways in which user data may be collected and/or generated consistently with this disclosure.

With continued reference to FIG. 1, computing device 104 may derive default enumeration from training set as a function of set of user data, using any suitable machine learning algorithm. As a non-limiting example, computing device 104 may derive default enumeration from training set using a lazy-learning process, and/or classification process, which may include any lazy-learning process and/or classification process as described above, including without limitation a K-nearest neighbors algorithm; K-nearest neighbors may return a single matching entry, or a plurality of matching entries. Where a plurality of matching entries are returned, computing device 104 may derive default enumeration from plurality of matching entries by aggregating user inclination enumerations of matching entries; aggregation may be performed using any suitable method for aggregation, including component-wise addition followed by normalization, component-wise calculation of arithmetic means, or the like. Persons skilled in the art, upon reviewing the entirety of this disclosure, will be aware of various ways in which multiple user inclination enumerations may be combined to create a default enumeration.

Still referring to FIG. 1, deriving the user inclination enumeration may additionally include displaying a default enumeration to the user. Default enumeration may be displayed to user via a user device. In an embodiment, display of default enumeration to user may be performed by populating data entry fields usable for user to enter values of user health vector with values taken from default enumeration. Such populated data entry fields may be displayed to user, indicating a first guess at user's likely preferences. Computing device 104 may receive a user command modifying the default enumeration; command may be received in the form of a modification and/or replacement by user of a value displayed in a user entry field. Computing device 104 may derive user inclination enumeration using the default enumeration and the user command; for instance, and without limitation, system may adopt user modifications to default enumeration to produce a user inclination enumeration.

Still referring to FIG. 1, user inclination enumeration may be stored in memory of computing device 104, including without limitation in user database 108 as described above. User inclination enumeration may be updated periodically; for instance a user may modify user inclination enumeration via a user interface, for instance to change one or more relative priorities to match user inclination enumeration. User may enter a command to view user inclination enumeration, modify one or more parameters and/or attributes of user inclination enumeration, and cause computing device 104 to store modified at least a user inclination enumeration.

With continuing reference to FIG. 1, assigning a degree of projected user adherence may include receiving a training set correlating a sets of individual user inclination enumerations and lifestyle intervention combinations with adherence data, where "adherence data" is defined for this purpose as data indicating a degree to which a user having a given user inclination enumeration adhered with a given lifestyle intervention combination; each element of adherence data may include an adherence score and/or other quantification of a degree to which a user adhered to the lifestyle intervention combination. Such elements of training data 124 may be received in any manner suitable for receipt of elements of training data 124 as described above, including without limitation expert inputs and/or user reported data. Computing device 104 may generate, using training set, an adherence score for each lifestyle intervention combination of plurality of lifestyle combinations as a function of a user inclination enumeration associated with the user. This may be performed using classification algorithms and/or classifiers, for instance and without limitation by representing lifestyle combinations and user inclination enumerations as vectors having corresponding attributes and determining a degree of proximity such as without limitation any measure of proximity as described above. Alternatively, training data 124 may be used to generate a machine-learning model, such as without limitation a regression model or other model representing a mathematical expression of training data 124 elements, which model outputs an adherence score quantifying degree of user adherence. However calculated, computing device 104 may assign degree of projected user adherence as a function of and/or using adherence score.

Still referring to FIG. 1, computing device 104 may alternatively or additionally assign a degree of projected user adherence by receiving a training set correlating a sets of user data and lifestyle intervention combinations with adherence data; training set may be generated using any process and/or process step described above, including without limitation user inputs and/or expert entries. Computing device 104 may generate, using the training set, an adherence score for each lifestyle intervention combination of the plurality of lifestyle combinations as a function of user data associated with the user; this may be performed as before using a classification algorithm and/or distance metric calculation, and/or using a machine-learning model generated as a function of the training data 124. User data may be received from a device operated by user and/or by querying user database 108. Computing device 104 may assign degree of projected user adherence as a function of the adherence score.

With continued reference to FIG. 1, computing device 104 may be configured to select a lifestyle intervention from the plurality of lifestyle intervention combinations as a function of the degree of projected user adherence of the selected lifestyle intervention combination. For instance, and without limitation, computing device 104 may select a lifestyle intervention combination having a maximal degree of projected user adherence. Alternatively or additionally, computing device 104 may rank intervention combinations according to projected degrees of user adherence and present two or more of the plurality of intervention combinations to user and/or via a computing device operated by user; user may select an intervention combination from the presented list of interventions and/or computing device 104 may receive a user selection of an intervention combination of the presented intervention combinations.

In an embodiment, and still referring to FIG. 1, before or after selection of a lifestyle intervention combination having a maximal degree of projected user adherence, computing device 104 may filter plurality of lifestyle intervention combinations by removing one or more lifestyle intervention combinations from plurality of lifestyle intervention combinations. This may be accomplished, without limitation, by receiving a user proscription, defined for purposes of this disclosure as any data indicating that an intervention element and/or lifestyle intervention combination is unsuitable for a user, identifying a lifestyle intervention combination of the plurality of lifestyle intervention combinations that conflicts with the user proscription, and eliminating the identified lifestyle intervention combination from the plurality of lifestyle intervention combinations. Identifying that lifestyle intervention combination conflicts with the user proscription may include identifying that the lifestyle intervention combination includes one or more intervention elements and/or combinations thereof that are forbidden by user proscription. User proscription may include a dietary restriction, allergy, food sensitivity, genetic condition such as phenylketonuria, or the like that prevents consumption of certain foods and/or classes of foods, an injury that prevents user from performing an exercise and/or class of exercises, or any other counterindication and/or user restriction as defined in this disclosure and/or in disclosures incorporated herein by reference. User proscription may include a user belief proscription, which is defined for purposes herein as a user proscription that prevents a user from engaging in a lifestyle intervention combination and/or intervention element because of religious and/or personal beliefs, such as without limitation dietary prohibitions imposed by kosher and/or halal belief systems and/or religious rules. Computing device 104 may be configured to identify a lifestyle intervention combination of the plurality of lifestyle intervention combinations that conflicts with the user belief proscription and eliminate the identified lifestyle intervention combination from the plurality of lifestyle intervention combinations. As noted above, each step of each process may be performed repeatedly and/or iteratively; for instance, one or more steps may be performed as part of a feedback loop wherein user activity and/or biological extractions are recorded, compared to lifestyle intervention combinations, and/or compared to previous biological extractions, and subsequent performance of any steps described in this description based on modified biological extraction and/or user activity information.

Figure 5:
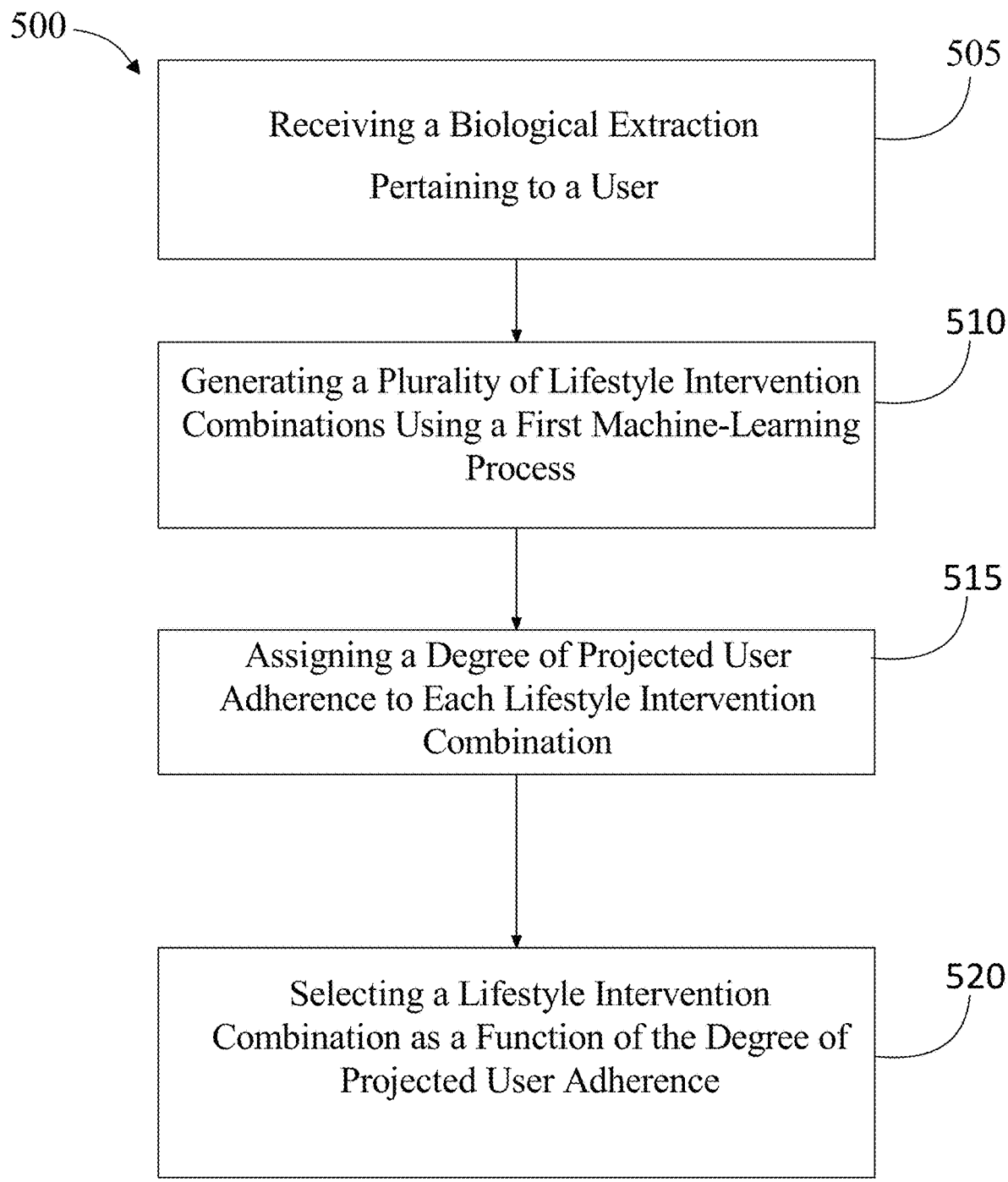
FIG. 5 is a flow diagram of an exemplary embodiment of a method generating lifestyle change recommendations based on biological extractions.

Referring now to FIG. 5, an exemplary embodiment of a method 500 of generating lifestyle change recommendations based on biological extractions is presented. At step 505, receiving, by a computing device, a biological extraction pertaining to a user; this may be performed, without limitation, as described above in reference to FIGS. 1-4.

Still referring at step 510, generating, by the computing device, and using a first machine-learning process 112, a plurality of lifestyle intervention combinations as a function of the biological extraction; this may be performed, without limitation, as described above in reference to FIGS. 1-4. Generating plurality of lifestyle intervention combinations may include receiving a description of at least a current disease state of the user and generating the plurality of lifestyle intervention combinations as a function of the current disease state. Generating plurality of lifestyle intervention combinations may include identifying a negative lifestyle behavior of the user and generating a plurality of lifestyle intervention combinations, wherein each lifestyle intervention combination alleviates the negative lifestyle behavior. Identifying the negative lifestyle behavior may include receiving a training set correlating biological extractions to negative lifestyle behaviors, generating a negative behavior identifier model using a supervised machine-learning algorithm and the training set, producing a negative lifestyle behavior output from the negative behavior identifier model using the biological extraction, and identifying the negative lifestyle behavior as a function of the negative behavior output.

At step 515, assigning, by a computing device and to each lifestyle intervention combination of the plurality of lifestyle intervention combinations, a degree of projected user adherence to the lifestyle intervention combination, wherein assigning further comprises performing a second machine learning process; this may be performed, without limitation, as described above in reference to FIGS. 1-4. Assigning degree of projected user adherence may include providing a user inclination enumeration, determining, using a classifier, a distance from the user inclination enumeration to each lifestyle intervention combination of the plurality of lifestyle intervention combinations, and assigning the degree of projected user adherence using the distance. Providing user inclination enumeration may include generating a default enumeration, displaying the default enumeration to the user, receiving a user command modifying the default enumeration, and deriving the user inclination enumeration using the default enumeration and the user command. Generating default enumeration may include receiving a training set correlating a cohort of individual information to individual user inclination enumerations, retrieving a set of user data regarding the user, and deriving the default enumeration from the training set as a function of the set of user data using a classification process. This may include receiving a training set correlating a sets of individual user inclination enumerations and lifestyle intervention combinations with adherence data generating, using the training set, an adherence score for each lifestyle intervention combination of the plurality of lifestyle combinations as a function of the user inclination enumeration, and assigning the degree of projected user adherence as a function of the adherence score. Assigning degree of projected user adherence may include receiving a training set correlating a sets of user data and lifestyle intervention combinations with adherence data and generating, using the training set, an adherence score for each lifestyle intervention combination of the plurality of lifestyle combinations as a function of user data of the user, and assigning the degree of projected user adherence as a function of the adherence score.

At step 520, and still referring to FIG. 5, computing device 104 may select, from the plurality of lifestyle intervention combinations, a lifestyle intervention combination as a function of the degree of projected user adherence to the selected lifestyle intervention combination; this may be performed, without limitation, as described above in reference to FIGS. 1-4. Computing device 104 may receive a user belief proscription, identify a lifestyle intervention combination of the plurality of lifestyle intervention combinations that conflicts with the user belief proscription, and eliminate the identified lifestyle intervention combination from the plurality of lifestyle intervention combinations.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
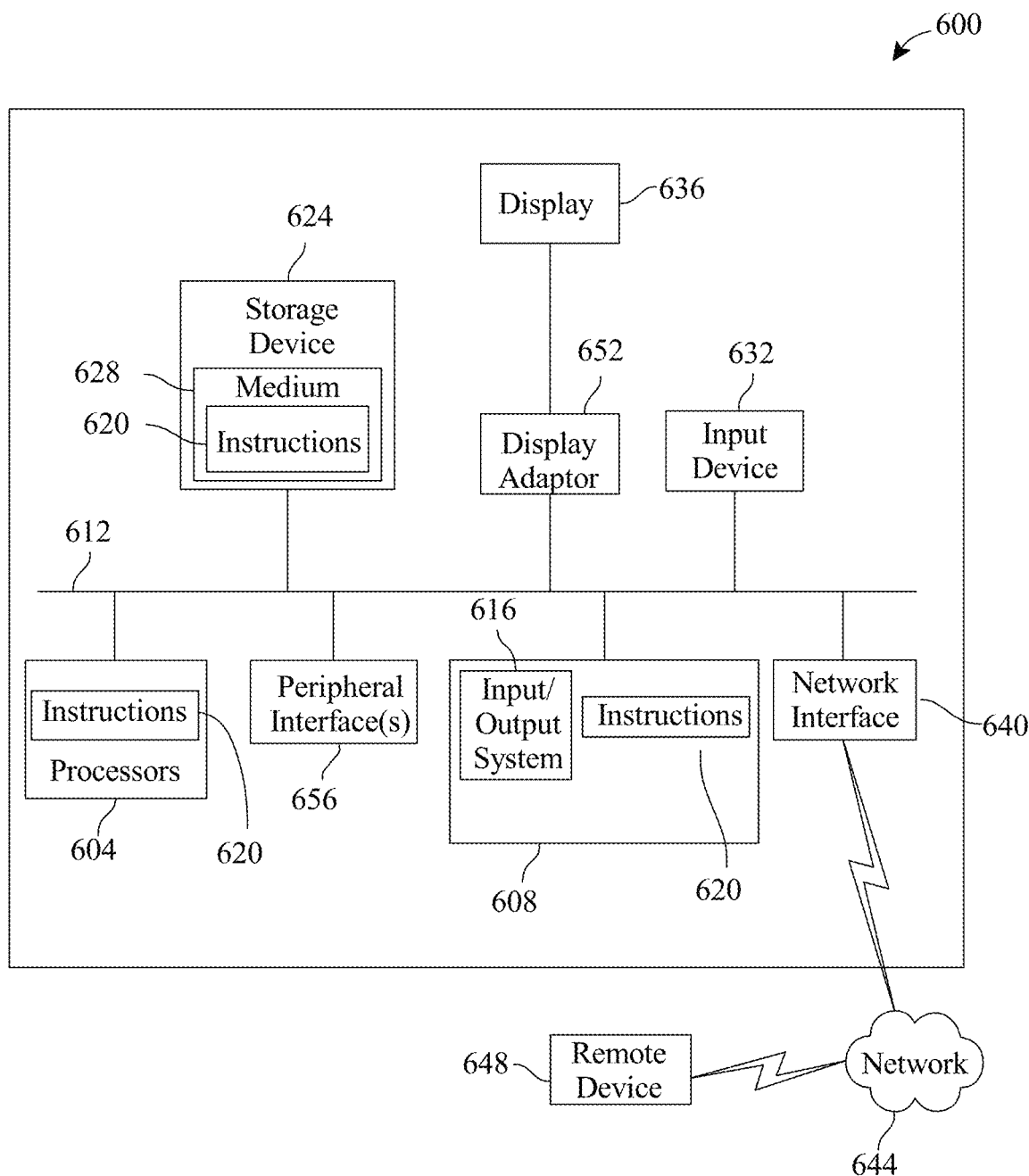
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating lifestyle change recommendations based on biological extractions, the system comprising a computing device, the computing device designed and configured to:

receive a biological extraction pertaining to a user, wherein the biological extraction comprises user physiological data comprising responses to a questionnaire;

generate a plurality of lifestyle intervention combinations as a function of the biological extraction using a first machine-learning process, wherein generating the plurality of lifestyle intervention combinations further comprises:

training a first machine-learning model using a first training data set and the first machine-learning process, wherein the first training data set comprises entries correlating biological extraction data with lifestyle intervention combinations; and utilizing the first machine-learning model to output the plurality of lifestyle intervention combinations using the biological extraction as an input;

derive a user inclination enumeration as a function of at least a user input, wherein the user inclination enumeration is a data structure that quantitatively measures a degree of importance a user places on a plurality of intervention elements;

assign, using a second machine-learning process, to each lifestyle intervention combination of the plurality of lifestyle intervention combinations, a projected degree of user adherence as a function of the user inclination enumeration, wherein assigning the degree of projected user adherence comprises:

training a second machine-learning model using a second training data set and the second machine-learning process, wherein the second training data set includes entries correlating lifestyle intervention combinations with adherence data; and utilizing the second machine-learning model to output the degree of projected user adherence using the plurality of lifestyle intervention combination as an input; and select, from the plurality of lifestyle intervention combinations, a lifestyle intervention combination as a function of the projected degree of user adherence of the selected lifestyle intervention combination.

2. The system of claim 1, wherein the biological extraction comprises a blood glucose measurement.

3. The system of claim 1, wherein the plurality of lifestyle intervention combinations comprises a recommended increase in consumption of foods tending to lower a glycemic index.

4. The system of claim 1, wherein the user physiological data further comprises a measurement of blood pressure.

5. The system of claim 1, wherein generating the plurality of lifestyle intervention combinations further comprises:

receiving, in the responses to the questionnaire, a description of at least a current disease state of the user; and generating the plurality of lifestyle intervention combinations as a function of the current disease state.

6. The system of claim 1, wherein the user physiological data further comprises one or more user-entered descriptions of a person's physiological state.

7. The system of claim 1, wherein the plurality of lifestyle intervention combinations comprises one or more particular forms of exercise.

8. The system of claim 1, wherein the plurality of lifestyle intervention combinations comprises an exercise program.

9. The system of claim 1, wherein the user inclination enumeration comprises a dietary elimination.

10. A method for generating lifestyle change recommendations based on biological extractions, the method comprising:

receiving, by a computing device, a biological extraction pertaining to a user, wherein the biological extraction comprises user physiological data comprising responses to a questionnaire;

generating, by the computing device, a plurality of lifestyle intervention combinations as a function of the biological extraction using a first machine-learning process, wherein generating the plurality of lifestyle intervention combinations further comprises:

training a first machine-learning model using a first training data set and the first machine-learning process, wherein the first training data set comprises entries correlating biological extraction data with lifestyle intervention combinations; and utilizing the first machine-learning model to output the plurality of lifestyle intervention combinations using the biological extraction as an input;

deriving, by the computing device, a user inclination enumeration as a function of at least a user input, wherein the user inclination enumeration is a data structure that quantitatively measures a degree of importance a user places on a plurality of intervention elements;

assigning, by the computing device using a second machine-learning process, to each lifestyle intervention combination of the plurality of lifestyle intervention combinations, a projected degree of user adherence as a function of the user inclination enumeration, wherein assigning the degree of projected user adherence comprises:

training a second machine-learning model using a second training data set and the second machine-learning process, wherein the second training data set includes entries correlating lifestyle intervention combinations with adherence data; and utilizing the second machine-learning model to output the degree of projected user adherence using the plurality of lifestyle intervention combination as an input; and selecting, by the computing device, from the plurality of lifestyle intervention combinations, a lifestyle intervention combination as a function of the projected degree of user adherence of the selected lifestyle intervention combination.

11. The method of claim 10, wherein the biological extraction comprises a blood glucose measurement.

12. The method of claim 10, wherein the plurality of lifestyle intervention combinations comprises a recommended increase in consumption of foods tending to lower a glycemic index.

13. The method of claim 10, wherein the user physiological data further comprises a measurement of blood pressure.

14. The method of claim 13, wherein the plurality of lifestyle intervention combinations comprises a recommended increase in consumption of foods tending to lower a glycemic index.

15. The method of claim 10, wherein the user physiological data further comprises one or more user-entered descriptions of a person's physiological state.

16. The method of claim 10, wherein generating the plurality of lifestyle intervention combinations further comprises:

receiving, in the responses to the questionnaire, a description of at least a current disease state of the user; and generating the plurality of lifestyle intervention combinations as a function of the current disease state.

17. The method of claim 10, wherein the plurality of lifestyle intervention combinations comprises one or more particular forms of exercise.

18. The method of claim 10, wherein the plurality of lifestyle intervention combinations comprises an exercise program.

19. The method of claim 10, wherein the user inclination enumeration comprises a dietary elimination.

* * * * *